United States Patent [19]

Baltes et al.

[11] 4,340,748

[45] Jul. 20, 1982

[54] PROCESS FOR THE MANUFACTURE OF GLYOXYLIC ACID ESTERS

[75] Inventors: Herbert Baltes, Frankfurt am Main; Ernst I. Leupold, Neu-Anspach; Friedrich Wunder, Flörsheim am main, all of Fed. Rep. of Germany

[73] Assignee: Hoechst Aktiengesellschaft, Frankfurt am Main, Fed. Rep. of Germany

[21] Appl. No.: 118,923

[22] Filed: Feb. 6, 1980

[30] Foreign Application Priority Data

Feb. 8, 1979 [DE] Fed. Rep. of Germany ....... 2904775

[51] Int. Cl.³ .................... C07C 67/313; C07C 69/67
[52] U.S. Cl. ..................... 560/177; 252/455 R; 252/461; 252/467; 252/468; 252/469; 252/475; 252/476; 562/577
[58] Field of Search ................ 560/177; 562/577; 252/455 R, 461, 467–469, 475–476

[56] References Cited

U.S. PATENT DOCUMENTS 1,627,091  5/1927  Haüssler et al. .................... 562/577

Primary Examiner—Vivian Garner
Attorney, Agent, or Firm—Curtis, Morris & Safford

[57] ABSTRACT

The invention relates to a process for the manufacture of glyoxylic acid esters by catalytic dehydrogenation of glycolic acid esters in the gaseous phase.

10 Claims, No Drawings

PROCESS FOR THE MANUFACTURE OF GLYOXYLIC ACID ESTERS

It is known from German Pat. No. 447.838 that hydroxycarboxylic acid esters can be dehydrogenated in the gaseous phase to oxocarboxylic acid esters in the presence of "oxides having an acidic character and which are derived from elements having several oxidation stages or of metal salts of acids derived from the said oxides".

In the sole detailed example using a hydroxycarboxylic acid ester, namely glycolic acid ethyl ester, a yield of about 50% of the theory is obtained. The reaction is carried out at elevated pressure. Selectivities, space-time-yields and time of contact are not defined in the specification.

With this relatively low yield, the product mixture obtained contains, besides the desired glyoxylic acid ester and water, considerable amounts of unreacted starting compound as co-product. In addition to the high amount of material required it is especially the expensive recycling of the unreacted glycolic acid ester involving important losses which impairs the economy of the process. In the distillation of the mixture formed of glycolic acid ester, glyoxylic acid ester and water a high proportion of the glycolic acid ester is reacted to give glycolide or it is hydrolyzed to glycolic acid.

It is the object of the present invention to provide a process for the manufacture of glyoxylic acid esters by dehydrogenation of glycolic acid esters in the gaseous phase in contact with a catalyst containing at least one of the elements V, Mo, Ag, Cu, which comprises passing the glycolic acid esters over the catalyst which contains in addition at least one of the following elements: Sn, Sb, Bi, elements of the first main group or elements of the second main group of the Periodic Table as promoter.

The oxides of Sn, Sb, Bi and the oxides of the elements of main groups I and II are basic or amphoteric (cf. A. F. Holleman and E. Wiberg, Lehrbuch der Anorganischen Chemie, 57th to 70th edition). In view of German Pat. No. 447,838, it is therefore surprising that catalysts containing, besides the elements V, Mo, Ag, Cu, additionally Sn, Sb, Bi, elements of main groups I and/or elements of main group II catalyze the dehydrogenation of glycolic acid esters with a high selectivity and high yields of glyoxylic acid esters not reached up to now.

In the process of the invention glycolic acid esters of the formula HO—$CH_2$—COOR are used in vapor form.

In the formula R denotes a hydrocarbon radical, preferably an aliphatic, straight chain or branched alkyl radical having from 1 to 8 carbon atoms, more preferably 1 to 5 carbon atoms.

The gaseous glycolic acid esters are passed over the catalyst either as such or, preferably, together with inert substances (inert under the chosen reaction conditions), for example water, alcohols, such as methanol or ethanol, chlorinated hydrocarbons such as chloroform, or chloroacetic acid esters. The addition of the inert substances considerably increases the selectivity.

The vaporous glycolic acid ester and inert substance, if any, are passed over the catalyst as such, preferably, however, together with a carrier gas such as nitrogen, nobel gases or lower saturated hydrocarbons, for example methane, ethane or propane.

It proved advantageous to add oxygen or an oxygen-containing gas, for example air, to the vaporous glycolic acid ester. If air is used, it acts simultaneously as carrier gas.

In the process according to the invention for each mol of glycolic acid ester the following amounts of additional substances are used:

0 to 10 mols of inert substance, preferably 0.01 to 2 mols; 0 to 5 mols of oxygen or oxygen-containing gas, preferably 0.1 to 3 mols;

0 to 80 mols of carrier gas, preferably 40 to 60 mols.

Satisfactory results may also be obtained with amounts outside the specified limits.

The catalyst contains at least one of the elements V, Mo, Ag, Cu (in the following designated as group A) and at least one of the elements (in the following designated as group B) Sn, Sb, Bi, elements of the first main group, and elements of the second main group, preferably Sn, Sb, Bi, K, Na, Li, Mg, and Ca. Elements of main groups III to V likewise exhibit a catalytic effect.

The aforesaid elements are used either in metallic form or in the form of their compounds such as the oxides, nitrates, acetates, acetylacetonates, oxalates, citrates or halides.

Prior to the introduction of the glycolic acid ester into the reaction zone, it proved advantageous to pass over the catalyst an oxidizing gas, preferably oxygen or air, or a reducing gas, preferably hydrogen or hydrogen diluted with inert gas at a temperature of from 100° to 800° C., preferably 300° to 600° C. The catalytically active elements are preferably supported on carrier materials. Suitable carrier materials are, above all, silicates, aluminum oxides, aluminum silicates, pumice or carbon, preferably silicates, aluminum oxides or aluminum silicates. Especially good results are obtained with aluminum silicates having a small BET surface area of less than 20 $m^2/g$, preferably less than 2 $m^2/g$.

The total amount of elements of groups A and B can vary within wide limits. In general, it is in the range of from 0.01 to 50% by weight, preferably 0.1 to 20% by weight, referred to the total amount of supported catalyst. The proportion of A to B is generally in the range of from 1:0.01 to 1:10, preferably 1:0.1 to 1:1. The catalytically active components are advantageously applied onto the carrier material in the form of a solution, the solvent is then evaporated and the catalyst is dried. Suitable solvents are water, hydrochloric acid, nitric acid, alkali metal hydroxide solutions, or aqueous ammonia solution, preferably, however, water.

It is also possible, of course, to use the active components per se without a carrier.

The process according to the invention is usually carried out at a temperature of from 100° to 600° C., preferably 200° to 400° C.

The time of contact is preferably in the range of from 0.1 to 10 seconds, more preferably 0.1 to 1 second. Outside the specified limits satisfactory results may also be obtained.

The process according to the invention is preferably carried out at atmospheric pressure, but reduced pressure or elevated pressure is also possible (0.01 to 100 bar).

To carry out the process of the invention the glycolic acid ester or the mixture of glycolic acid ester and inert substances is introduced in dosed quantities by means of a dosing device into an evaporation zone and the gas mixture formed is passed through a reaction tube containing the catalyst and provided with external heating means. In the evaporation zone the gas mixture is optionally blended with the carrier gas and/or oxygen or oxygen-containing gas. It proved advantageous to heat the gases to the reaction temperature prior to mixing.

After having left the reactor, the reaction mixture is cooled to separate the condensable portions. The pure glyoxylic acid ester can be separated by distillation from the condensate.

Because of their high reactivity glyoxylic acid esters constitute valuable starting products and intermediates for various syntheses of pharmaceutically active compounds, for example allantoin, substituted glycines or alkaloids (for example tetrahydroisoquinoline-alkaloids).

The following examples illustrate the invention.

EXAMPLE 1

By means of a syringe fitted with plunger 6 ml/hr of glycolic acid methyl ester are introduced into an evaporation zone and passed from there into a vertical glass reactor having a length of 150 mm and a diameter of 20 mm. Simultaneously 56 Nl/hr of nitrogen and 1.6 Nl/hr of oxygen, both heated to 300° C., are fed to the evaporation zone.

The reactor is heated from the outside to 300° C. and contains 15 ml of an aluminum silicate carrier catalyst having a BET surface of about 1 $m^2/g$ and being impregnated with 7.0% by weight of Sn and 3.0% by weight of V. To prepare the carrier catalyst 1.4 g of ammonium vanadate are dissolved in 25 ml of water and 18 g of carrier material are impregnated therewith. Next, the solvent is evaporated on the steam bath. In the same manner the carrier catalyst is impregnated with a solution of 2.2 g of $SnCl_2$ in 5 ml of water. The catalyst is then dried at 110° C. and heated in the reactor for 3 hours at 400° C. in a gas current of 1 Nl/hr of oxygen and 56 Nl/hr of nitrogen. The temperature in the reactor is measured with a thermocouple. The reaction products are condensed in a cooling trap at −70° C.

After a starting period of 1 hour to adjust constant conditions of operation, the reaction proper is carried out over a period of 2 hours. The condensate is analyzed by liquid chromatography.

After a reaction period of 2 hours, 137 mmols of glyoxylic acid methyl ester, corresponding to a yield of 88.3% and a selectivity of 89%, are found.

EXAMPLE 2

In the manner described in Example 1 the device described in said example is charged with 6 ml/hr of glycolic acid methyl ester, 1 ml/hr of methanol and 15 Nl/hr of air. The reactor contains the same catalyst as in Example 1 but is heated to 250° C.

After a reaction period of 2 hours, 102 mmols of glyoxylic acid methyl ester, corresponding to a selectivity of 95%, are obtained.

EXAMPLE 3

In the manner described in Example 1, the device described in said example is charged with 6 ml/hr of glycolic acid methyl ester, 1 ml/hr of water, 0.82 Nl/hr of oxygen and 56 Nl/hr of nitrogen. The reactor contains 15 ml of an aluminum silicate supported catalyst impregnated with 5.8% by weight of V, 3.2% by weight of Sn, 0.5% by weight of K and 0.5% by weight of Mg on a carrier as described in Example 1. The reactor is heated to 250° C.

After 2 hours the condensate contains 107 mmols of glyoxylic acid methyl ester, corresponding to a selectivity of 92%.

EXAMPLE 4

In the manner described in Example 1, 9 ml/hr of glycolic acid methyl ester, 0.82 Nl/hr of oxygen and 56 Nl/hr of nitrogen are introduced into the device described in said example. The reactor is charged with 15 ml of an aluminum silicate carrier catalyst containing 7.1% by weight of Sb and 2.9% by weight of V and having a BET surface of about 12 $m^2/g$. The temperature in the reactor is 350° C.

After a reaction time of 2 hours the condensate contains 143 mmols of glyoxylic acid methyl ester, corresponding to a selectivity of 70%.

EXAMPLE 5

In the manner described in Example 1, a mixture of 6 ml/hr of glycolic acid methyl ester, 0.5 ml/hr of chloroacetic acid methyl ester, 0.82 Nl/hr of oxygen and 56 Nl/hr of nitrogen are introduced into the device as described. The reactor is charged with 15 ml of an aluminum silicate catalyst containing 5.5% by weight of Sn and 4.5% by weight of Mo applied onto a carrier as specified in Example 1. The reactor is heated to 300° C.

After 2 hours 122 mols of glyoxylic acid methyl ester are obtained, corresponding to a yield of 78.4% and a selectivity of 84%.

EXAMPLE 6

In the manner described in Example 1, 6 ml/hr of glycolic acid methyl ester, 1.6 Nl/hr of oxygen and 56 Nl/hr of nitrogen are introduced into the device as described. The reactor is charged with 15 ml of a carrier catalyst containing 3.5% by weight of Ba, 5.5% by weight of V and 1.0% by weight of Na supported on a carrier as specified in Example 1. The temperature in the reactor is 250° C.

After 2 hours the condensate contains 103 mmols of glyoxylic acid methyl ester, corresponding to a selectivity of 87%.

EXAMPLE 7

In the manner described in Example 1, 6 ml/hr of glycolic acid methyl ester, 1.6 Nl/hr of oxygen and 56 Nl/hr of nitrogen are introduced into the reactor as described. The reactor is charged with 15 ml of an aluminum silicate carrier catalyst containing 7.5% by weight of V, 1.0% by weight of Mg, 1.0% by weight of K and 0.5% by weight of Li supported on a carrier as specified in Example 1. The temperature in the reactor is 300° C. After 2 hours 67 mmols of glyoxylic acid methyl ester are obtained, corresponding to a selectivity of 64%.

EXAMPLE 8

In the manner described in Example 1, 6 ml/hr of glycolic acid ethyl ester, 1 ml/hr of ethanol and 15 Nl/hr of air are introduced into the device as described. The reactor is charged with 15 ml of an aluminum silicate carrier catalyst containing 4.2% by weight of Sn, 3.6% by weight of V and 2.2% by weight of Cu supported on a carrier as defined in Example 1. The temperature in the reactor is 250° C.

After 2 hours 77 mmols of glyoxylic acid ethyl ester are obtained, corresponding to a selectivity of 89%.

EXAMPLE 9

In the manner described in Example 1, 6 ml/hr of glycolic acid n-butyl ester, 1.0 Nl/hr of oxygen and 56 Nl/hr of nitrogen are introduced into the device as described. The reactor is charged with 15 ml of an aluminum silicate carrier catalyst containing 8.05% by weight of Bi and 1.95% by weight of V applied onto a carrier as defined in Example 1. The temperature in the reactor is 250° C.

After a reaction time of 2 hours the condensate contains 39.5 mmols of glyoxylic acid n-butyl ester, corresponding to a selectivity of 83%.

EXAMPLE 10

In the manner described in Example 1, 9 ml/hr of glycolic acid n-butyl ester and 56 Nl/hr of nitrogen are introduced into the apparatus as described. The reactor is heated to 300° C. It is charged with 15 ml of an aluminum silicate carrier catalyst containing 6.6% by weight of Sb and 3.4% by weight of Cu on a carrier as defined in Example 1.

After 2 hours the condensate contains 36 mmols of glyoxylic acid n-butyl ester (selectivity 45%).

EXAMPLE 11

In the manner described in Example 1, 9 ml/hr of glycolic acid n-butyl ester, 0.5 ml/hr of chloroform and 15 Nl/hr of air are introduced into the apparatus as described. The reactor is heated to 250° C. and charged with 15 ml of an aluminum silicate carrier catalyst containing 4.2% by weight of Sn, 3.6% by weight of V and 2.2% by weight of Ag applied onto a carrier as defined in Example 1.

After a time of reaction of 2 hours the condensate contains 60 mmols of glyoxylic acid n-butyl ester, corresponding to a selectivity of 85%.

We claim:

1. A process for the manufacture of a glyoxylic acid ester by dehydrogenation of a glycolic acid ester in the gaseous phase which comprises contacting said glycolic acid ester with a catalyst containing, as an active component, V, Mo, Ag, Cu, or a combination thereof, and a catalytic promoter containing an effective amount of at least one element selected from the group consisting of Sn, Sb, Bi, elements of Group IA and elements of Group IIA of the Periodic Table.

2. The process of claim 1 in which said catalytic promoter contains at least one element selected from the group consisting of Sn, Sb, Bi, K, Na, Li, Mg and Ca.

3. The process of claim 1 wherein said active component and catalytic promoter are combined in a weight ratio in the range of 1:0.01 to 1:10.

4. The process of claim 1, 2 or 3 which further comprises contacting a mixture of glycolic acid ester and an inert substance selected from the group consisting of water, alcohols, chlorinated hydrocarbons and chloroacetic acid esters with said catalyst.

5. The process of claim 1, 2 or 3 in which the catalyst is applied onto an aluminum silicate carrier having a BET surface of less than 20 $m^2/g$.

6. The process of claim 1 wherein the dehydrogenation is conducted at a temperature in the range of 100° C. to 600° C.

7. The process of claim 1 wherein the dehydrogenation is conducted at a temperature in the range of 200° C. to 400° C.

8. A process for the manufacture of a glyoxylic acid ester by dehydrogenation of a glycolic acid ester in the gaseous phase which comprises contacting a mixture of glycolic acid ester, an inert substance selected from the group consisting of water, alcohols, chlorinated hydrocarbons and chloroacetic acid esters, oxygen or an oxygen-containing gas and a carrier gas at a molar ratio of 0.01 to 2 mols inert substance, 0.1 to 3 mols oxygen or oxygen-containing gas and 40 to 60 mols of carrier gas per mol of glycolic acid ester, with a catalyst containing, as an active component, V, Mo, Ag, Cu, or a combination thereof, and a catalytic promoter containing an effective amount of at least one element selected from the group consisting of Sn, Sb, Bi, elements of Group IA and elements of Group IIA of the Periodic Table.

9. The process of claim 8 in which the dehydrogenation is conducted at a temperature in the range of 200° C. to 400° C.

10. The process of claim 8 in which the carrier gas is nitrogen, a noble gas or lower saturated hydrocarbon.

* * * * *